(12) United States Patent
Atkins et al.

(10) Patent No.: US 11,554,036 B2
(45) Date of Patent: Jan. 17, 2023

(54) DEVICES AND METHODS FOR NASAL SPLINTING

(71) Applicant: TACKLEBOX MEDICAL, LLC, Mountain View, CA (US)

(72) Inventors: James H. Atkins, San Antonio, TX (US); Celso Bagaoisan, Union City, CA (US); Suresh S. Pai, Los Altos, CA (US)

(73) Assignee: TACKLEBOX MEDICAL, LLC, Mountain View, CA (US)

(*) Notice: Subject to any disclaimer, the term of this patent is extended or adjusted under 35 U.S.C. 154(b) by 317 days.

(21) Appl. No.: 16/740,337

(22) Filed: Jan. 10, 2020

(65) Prior Publication Data
US 2020/0214871 A1 Jul. 9, 2020

Related U.S. Application Data

(63) Continuation of application No. 14/991,672, filed on Jan. 8, 2016, now Pat. No. 10,531,975, which is a continuation of application No. PCT/US2014/045816, filed on Jul. 8, 2014.

(60) Provisional application No. 61/843,841, filed on Jul. 8, 2013.

(51) Int. Cl.
*A61F 5/08* (2006.01)
*A61B 17/24* (2006.01)
*A61F 5/058* (2006.01)

(52) U.S. Cl.
CPC ........... *A61F 5/08* (2013.01); *A61B 17/24* (2013.01); *A61F 5/05891* (2013.01)

(58) Field of Classification Search
CPC ......... A61F 5/08; A61F 5/05891; A61B 17/24
See application file for complete search history.

(56) References Cited

U.S. PATENT DOCUMENTS

| 3,935,859 | A | * | 2/1976 | Doyle | A61F 5/05891 606/199 |
|---|---|---|---|---|---|
| 4,105,035 | A | * | 8/1978 | Rella | A61F 5/08 606/199 |
| 4,592,357 | A | * | 6/1986 | Ersek | A61F 5/08 606/199 |
| 5,350,396 | A | * | 9/1994 | Eliachar | A61F 5/08 602/17 |
| 6,186,965 | B1 | * | 2/2001 | Patterson | A61B 17/0401 602/5 |
| 2009/0143821 | A1 | * | 6/2009 | Stupak | A61B 17/24 606/228 |

(Continued)

*Primary Examiner* — Alexander J Orkin
(74) *Attorney, Agent, or Firm* — William A. English; Vista IP Law Group LLP

(57) ABSTRACT

A nasal splint and methods for using such splints are provided. The nasal splint may include an elongate generally planar member comprising first and second ends, and a first outer surface and an opposite second outer surface; a tubular airway extending along the first outer surface at least partially between the first and second ends, thereby defining a lumen having an opening adjacent the first end; and a structure on one of the elongate member and tubular airway adjacent the first end supporting a feature that is spaced apart from the first outer surface and configured to support a suture across the opening when the suture is directed through the elongate member adjacent the first end and the feature.

16 Claims, 8 Drawing Sheets

(56) References Cited

U.S. PATENT DOCUMENTS

2009/0248058 A1\* 10/2009 Kotler ............... A61M 16/0666
                                                        606/199
2010/0049247 A1\* 2/2010 Larkin ................... A61B 50/30
                                                        606/232
2012/0071913 A1\* 3/2012 Tamez ...................... A61F 5/08
                                                        606/199

\* cited by examiner

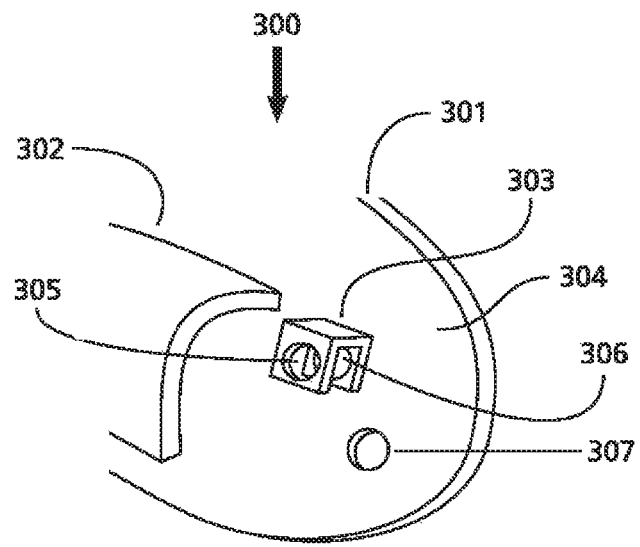
FIG. 7A
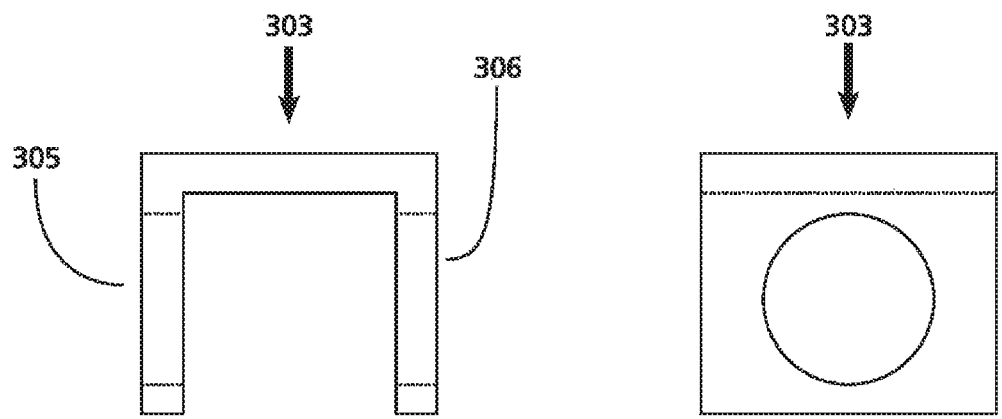
FIG. 7B
FIG. 7C

DEVICES AND METHODS FOR NASAL SPLINTING

RELATED APPLICATION DATA

This application is a continuation of co-pending application Ser. No. 14/991,672, filed Jan. 8, 2016, issuing as U.S. Pat. No. 10,531,975, which is a continuation of International Application No. PCT/US2014/045816, filed Jul. 8, 2014, which claims benefit of provisional application Ser. No. 61/843,841, filed Jul. 8, 2013, the entire disclosures of which are expressly incorporated by reference herein.

FIELD OF THE INVENTION

The present invention relates to devices and methods for performing surgical procedures, and more particularly to splint devices and methods for performing septoplasty and/or other nasal surgery, which may involving locating and/or removing one or more sutures.

BACKGROUND

The use of splints and other reinforcing materials to maintain the position of tissues following surgery is a common technique in medicine. These structures are often secured in position using a suture tied to the surrounding tissue or tissues. Thin gauge suture material is used to minimize scarring and disruption to the anchoring tissue. While successful in doing so, the use of small-diameter suture material can introduce some difficulties when the splints are to be removed during the course of a patient's recovery. Thin suture material can be difficult to identify and isolate at the healing surgical site, leading to a potentially painful and cumbersome excavation procedure (patients are awake at the follow-up visits when the splints or reinforcing materials are removed). The devices and methods describe herein may simplify the identification and cutting of suture materials used to fix splints, stents, reinforcing materials, and the like in position at a surgical site.

As an example, septoplasty, or the surgical correction of problems of the nasal septum, is a procedure commonly performed to address a number of issues that can affect the quality of a patient's life. For example, the procedure may involve repairing a defect to the septum that is partially or fully occluding the airways in the nose (e.g., a deviated septum, in which the nasal septum does not equally divide the nasal cavity into two halves), uncontrollable nosebleeds, and to repair a hole in the nasal septum (i.e., a nasal perforation).

To perform a septoplasty, a surgeon generally makes an incision on one side of the nasal septum, lift the mucus membrane that covers the septum off of the cartilage and/or bone of the nasal septum, remove, modify, or move the structures of the nasal septum that are causing the patient's symptoms, and replace the mucus membrane over the surgically-altered structure of the nasal septum. The membrane may be held in place using sutures, splints, packing materials, or a combination thereof.

The maintenance of a midline orientation of the septum (dividing the nasal cavity into two approximately equal halves) is the prime goal following septoplasty. Nasal splints are commonly used to achieve this end. The placement of a splint on each side of the septum keeps it aligned during the critical healing period immediately following surgery. These splints are typically shaped and sized to support the septum and provide a clear airway during the recovery period, and are supplied in pairs (each individual unit configured for placement on the right or left side of the nasal septum). Splints of this nature are typically sutured to the nasal septum through the proximal end of the splints. One suture is used to bind both splints to the nasal septum; this is done by passing a suture needle through one splint, starting from the face situated away from the septum, through the septum, through the second splint on the other side of the septum, and back through the septum proximal to the splints. The two free ends of the suture are then tied off to maintain the position of the splints with respect to the nasal septum, while the size and structure of the splints maintain the position of the nasal septum with respect to the nasal cavity.

A common commercially available nasal splint is the Doyle splint. The basic design of the Doyle splint is disclosed in U.S. Pat. No. 3,935,859 and remains one of the most used nasal splints following septoplasty. The Doyle splint includes a flat plate contoured to accommodate the nasal septum and an integral tube running the length of the flat plate opposite to the side of the plate that would rest against the nasal septum. The top edge of the plate has a convex curve and the bottom edge of the plate is slightly concave. The anterior and posterior ends of the plate are rounded to provide ease of insertion and patient comfort. The tube extends almost the full length of the splint and provides a passageway for airflow.

The anterior ends of a pair of Doyle splints are typically sutured to the nasal septum after placement against the surgically repaired nasal septum (one splint on each side of the septum). Once the position of the Doyle splints has been secured with the suture, the spaces surrounding the splint are sometimes packed with gauze or other materials to fully support the septum. The presence of the tube allows the patient to breath while the packing material is resident.

Variations of the Doyle splint include the Breeze Nasal Airway Splint (Summit Medical), the Nasal Airway Splint, Doyle Open Lumen Splint, Doyle Combo Splint (Boston Medical Products), and the Doyle Bi-Valve Airway Splint (Medtronic), which add or change features of the original Doyle splint, but all are sutured into position in a similar fashion after placement. Other nasal splint designs exist that eliminate the tube feature of the Doyle-style splints, add pre-formed holes intended to facilitate placement of the suture, and/or change the geometry of the flat plate, but these too require fixation with a suture after the splint is placed in the patient.

The use of a suture to secure the position of existing splints may cause difficulties when the splints are removed at a post-surgical follow-up exam. At a typical follow up visit, the surgeon cuts the suture holding or securing the splints against the septum. This procedure can be difficult to perform while the patient is awake as the post-surgical mucosal surfaces of the nasal cavity may be very sensitive to touch. Patients often move while the surgeon is attempting to locate and cut/release the suture. The procedure is further complicated by the tight apposition of the splint to the septum. Finding the suture can be difficult due to the small diameter or gage of the suture material that is typically used in these procedures (e.g., 3-0 silk) and the presence of encrustations of dried mucus and blood that can cover and obscure the suture site. Once found, positioning the surgical scissors to cut the suture without harming or causing discomfort to the patient can be a difficult and time-consuming task.

While existing nasal splints serve the purpose of supporting the septum and maintaining an open airway to the nasal cavity, there is a need for an intranasal splint that facilitates locating and cutting a stabilizing suture at the time of removal.

SUMMARY

The present invention is directed to devices and methods for performing surgical procedures, and more particularly to splint devices for performing septoplasty and/or other nasal surgery that may involve locating, cutting, and/or otherwise removing one or more sutures.

In accordance with one embodiment, a nasal splint is provided that includes a member having a first outer planar surface and an opposite second outer planar surface separated by a wall; a tubular airway connected to the first outer planar surface on a line substantially parallel to a longitudinal axis extending from a first end of the member to a second end of the member; an aperture located proximal to the first end of the member; a structure located proximal to the first end of the member, wherein the structure is configured to provide a space between a suture and the first outer planar surface of the member, and along the length where the suture traverses between the aperture and the structure.

The member, tubular airway, and structure may be fabricated as one integrated part or may be fabricated separately and joined together using methods known in the art, such as one or more of injection molding, casting, over-molding, welding, ultrasonic welding, adhesive bonding, solvent bolding, combinations thereof, and the like. The tubular member may also include at least one lumen extending from the first end to the second end of the tubular member if desired. The member and tubular airway may be constructed of materials known in the art, e.g., including one or more of medical grade silicone, polytetrafluoroethylene, polyethylene terephthalate, polyether ether ketone, polyamide, polyoxymethylene (acetal), polyether block amide, polyurethane, polypropylene, polyvinyl chloride, polyester, combinations thereof, and the like. The structure may be of equal or greater stiffness than the member and/or tubular airway, and may be fabricated from materials known in the art, e.g., including one or more of medical grade silicone, polytetrafluoroethylene, polyethylene terephthalate, polyether ether ketone, polyamide, polyoxymethylene, polyether block amide, polyurethane, polypropylene, polyvinyl chloride, polyester, polycarbonate, acrylic, acrylonitrile butadiene styrene, natural rubber, stainless steel, titanium, nickel, platinum, combinations or alloys thereof, and the like.

In an exemplary embodiment, the structure may have a shape that is substantially circular with a given length or ring-shaped. Alternatively, the structure may be non-circular or irregularly shaped, and/or may be shaped to substantially match and/or conform to the shape of the airway. The structure may also include two holes located at opposite sides of the ring (e.g., offset one hundred eighty degrees (180°) away from each other). The holes may be sized such that a suture needle may pass through each of the holes. The structure may be aligned concentrically with the distal (or anterior) end of the tubular airway such that the structure is aligned along the interior wall of the tubular airway and the lumen of the ring communicates with the lumen of the tubular airway.

The structure may be joined to the tubular airway by methods known to the art including one or more of press fitting, welding, casting, over-molding (e.g., the tubular airway and member are over-molded around the structure), adhesive bonding, combinations thereof, and the like. The structure may be radially aligned such that a line drawn through the first and second holes is perpendicular to the plane of the member, with the first hole adjacent to the member and the second hole adjacent to the wall of the tubular airway opposite the first hole. While this example describes holes arranged in a single specific manner, it should be clear to one of skill in the art that the holes may be arranged at any location in or around the structure. Furthermore, it should be clear to one of skill in the art that the number of holes in the structure is not limited to two, and the holes may be of different or identical shapes and sizes. For example, the first hole may be a channel arranged parallel or perpendicular to the longitudinal axis of the member and the second hole may be substantially circular. It should be clear that other sizes, shapes, orientation, and locations of the holes in the structure may be included in the devices described herein.

In a typical procedure, two symmetrical splints are used to stabilize and support the nasal septum. In the procedure, a suture needle with suture is inserted through the first and second holes in the structure and then through the member of the first splint. The suture needle with suture then pierces through the patient's nasal septum and exits on the far side of the nasal septum. The suture needle with suture then passes through the member of the second splint and then continues through the second and first holes of the structure of the second splint. Then, the suture needle with suture may then be passed back through the distal end of the member of the second splint across the nasal septum and through the distal end of the member of the first splint to be tied off and/or otherwise secured.

Alternatively, if only one splint is used, a suture needle with suture is inserted through the first and second holes in the structure and then through the member of the first splint. The suture needle with suture then pierces through the patient's nasal septum and exits on the far side of the nasal septum. Then, the suture needle with suture may be passed back through the nasal septum and through the distal end of the member of the first splint to be tied off and/or otherwise secured.

In the above described procedural steps using any of the embodiments of the devices described herein, the suture is suspended in the lumen of the tubular airway of the splint(s) to allow easy access with surgical scissors or any other cutting tools or instruments to facilitate simple splint removal. The stiffness of the structure may be such that when the suture is tightened and tied off, the tubular airway remains patent (i.e., is not constricted or closed off). In another example, additional holes may be pre-formed or placed in the wall of the tubular airway and member that align with the holes in the structure to ease placement of the suture. These holes may be fabricated using methods known in the art, e.g., including one or more of mechanical cutting and/or drilling, melting, laser cutting, mechanical punching, casting, injection molding (e.g., formed in the same mold as the member and tubular airway), combinations thereof, and the like.

Alternatively, the lumen of the structure may remain concentrically aligned with the lumen of the tubular airway yet offset a given distance proximal or distal to the distal end of the tubular airway. In the case that the structure is distally offset from the distal end of the tubular member, the structure may be joined to the member using methods known in the art, e.g., including one or more of welding, casting, over-molding (e.g., the tubular airway and member may be over-molded around the structure), adhesive bonding, combinations thereof, and the like.

In yet another example, the structure may have other geometries including one or more of arcs, hooks, ellipses, rectilinear shapes, combinations thereof, and the like. Furthermore, the structure may be sized to be smaller or larger than the lumen of the tubular airway and/or not concentrically aligned with the tubular airway. In one example, the structure may be substantially circular in geometry with two opposed holes as previously disclosed, but smaller in size than the lumen of the tubular airway and tangent to and in contact with the member.

In another embodiment, a hook may be anchored in the wall and/or extending into the lumen of the structure instead of the second hole in the structure. For illustrative purposes, the structure is assumed to be substantially circular in shape, however, it should be clear to one of skill in the art that the structure may assume other geometries. The hook may be oriented with the open portion of the hook facing towards the top of the structure. In this embodiment, the suture may be looped over the hook instead of passed through the wall of the tubular airway and the second hole in the structure. The hook feature may provide the operator with a quicker method for placing the suture and/or may simplify the procedure. It should be noted that all previously disclosed aspects are contemplated for this embodiment.

In yet another embodiment, the structure may include a tubular passage including a distal and proximal end and at least one lumen extended therethrough joined to the distal edge of the tubular airway. The tubular passage may be of equal or greater stiffness than the member and/or tubular airway, and may be fabricated from materials known in the art, e.g., including one or more of medical grade silicone, polytetrafluoroethylene, polyethylene terephthalate, polyether ether ketone, polyamide, polyoxymethylene, polyether block amide, polyurethane, polypropylene, polyvinyl chloride, polyester, polycarbonate, acrylic, acrylonitrile butadiene styrene, natural rubber, stainless steel, titanium, nickel, platinum, combinations or alloys thereof, and the like. The tubular passage may be connected to the tubular airway using methods known to the art including one or more of press fitting, welding, casting, over-molding (e.g., the tubular airway and member may be over-molded around the structure), adhesive bonding, combinations thereof, and the like. The tubular passage may further extend along the perimeter of the distal edge of the tubular airway. The internal diameter of the tubular passage may be sized to accept standard sizes of suture needles.

For example, if the cross section of the tubular airway is D-shaped with the flat edge of the "D" shape coincident to the surface of the member, the tubular passage may be an arc starting at the start of the midpoint of the curved portion of the "D," extending upward along the edge of the tubular airway to the top of the "D" and terminating substantially perpendicular to the flat edge of the "D." A suture needle may be inserted in the entrance of the tubular member and advanced through and exit the tubular member, pierce the wall of the tubular airway and member, and pass through and exit the nasal septum.

If desired, the suture may be passed through a second symmetrical version of this embodiment on the opposite nasal passage (i.e., traversing the member, wall of the tubular airway, the tubular passage, and the lumen of the tubular airway). The needle may then be passed back through the member of the second splint, the nasal septum, and the member of the first nasal splint distal to the structure and tied off, e.g., to suspend the suture thread in the middle of the tubular airways of the first and second splints. Either one or both of the tubular airway and member may also include one or more holes or apertures to facilitate the passage of the suture needle and subsequent securing of the device to the nasal septum.

The tubular passage of this embodiment may be a continuous closed passage, or may be a series of rings or braces of other geometries. For example, the tubular passage may be a single ring that is of a length considerably shorter than the perimeter of a cross-section of the tubular airway. Furthermore, the tubular passage may be a ridge or curved segment that does not close completely at all points along the length of the tubular passage. As an example, the tubular passage may define an arc of about two hundred seventy degrees (270°) in cross section. In another example the tubular passage may define an arc of about two hundred seventy degrees) (270°) in cross section with one or more segments that are a circle in cross section.

While some of the preceding examples have described the tubular airway as a member with a lumen, it should be clear that the features of the devices described herein are equally applicable to other splinting or stenting configurations. For example, the tubular airway may be a flange that is affixed to and aligned substantially parallel to the longitudinal axis of the member, and in cross section forms an arc that curves down and away from the member until the lower portion of the flange is substantially parallel to the face of the member.

Another embodiment of a nasal splint that is contemplated is a member having a first outer planar surface and an opposite second outer planar surface. This member may be placed between tissues to prevent the formation of adhesions and/or to support said tissues during the healing period. The structures previously described may be combined with the member to allow for easier location and cutting of a suture thread.

In accordance with an exemplary embodiment, a nasal splint is provided that includes an elongate generally planar member comprising first and second ends, and a first outer surface and an opposite second outer surface extending between the first and second ends; a tubular airway extending along the first outer surface at least partially between the first and second ends, thereby defining an airway lumen having an opening adjacent the first end; and a protrusion extending from the tubular airway adjacent the first end such that a free end of the protrusion is spaced apart from the first outer surface to support a suture at least partially across the opening when the suture is directed through the elongate member.

Optionally, the free end of the protrusion may include one of a hole, a hook, and a weakened region to receive a needle and suture therethrough. In addition or alternatively, the first end of the elongate member comprises a hole or weakened region adjacent the protrusion to receive a suture therethrough such that the suture extends across the lumen between the hole or weakened region and the protrusion.

In accordance with another embodiment, a nasal splint is provided that includes an elongate generally planar member comprising first and second ends, and a first outer surface and an opposite second outer surface extending between the first and second ends; a tubular airway extending along the first outer surface at least partially between the first and second ends, thereby defining a lumen having an opening adjacent the first end; and a bracket extending from one of the elongate member and tubular airway adjacent the first end and one of a hole and a weakened region on the bracket disposed adjacent the opening and spaced apart from the first outer surface to support a suture at least partially across the opening when the suture is directed through the elongate member and through the one of a hole and a weakened region.

In accordance with still another embodiment, a nasal splint is provided that includes an elongate generally planar member comprising first and second ends, and a first outer surface and an opposite second outer surface extending between the first and second ends; a tubular airway extending along the first outer surface at least partially between the first and second ends, thereby defining a lumen having an opening adjacent the first end; and a hook extending from one of the elongate member and tubular airway adjacent the first end, the hook disposed adjacent the opening and spaced apart from the first outer surface to support a suture at least partially across the opening when the suture is directed through the elongate member and the hook.

In accordance with yet another embodiment, a method is provided for treating a patient that includes inserting a nasal splint into the patient's sinus, the nasal splint comprising an elongate planar member and an airway lumen extending along a first surface of the elongate member; positioning a second surface of the elongate member against the sinus septum such that the airway lumen extends along the patient's sinus; and directing a suture through the patient's septum, the elongate member, and a structure on the nasal splint such that the suture extends across a portion of the airway lumen.

Other aspects and features of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of various features are arbitrarily expanded or reduced for clarity. Included in the drawings are the following figures:

FIG. 7A is a perspective view of a distal section of another exemplary embodiment of a nasal splint.

FIGS. 7B and 7C are front and side view of a structure that be included in the nasal splint shown in FIG. 7A.

DETAILED DESCRIPTION OF THE EXEMPLARY EMBODIMENTS

Before the exemplary embodiments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the embodiments described, subject to any specifically excluded limit in the stated range. Where the stated range includes one or both of the limits, ranges excluding either or both of those included limits are also included in the embodiments described.

Unless defined otherwise, all technical and scientific terms used herein have the same meaning as commonly understood by one of ordinary skill in the art to which the devices and methods herein belong. Although any methods and materials similar or equivalent to those described herein may be used in the practice or testing of the devices and methods herein, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

The publications discussed herein are provided solely for their disclosure prior to the filing date of the present application. Nothing herein is to be construed as an admission that the devices and methods described and claimed herein are not entitled to antedate such publication. Further, the dates of publication provided may be different from the actual publication dates, which may need to be independently confirmed.

Figure 1:
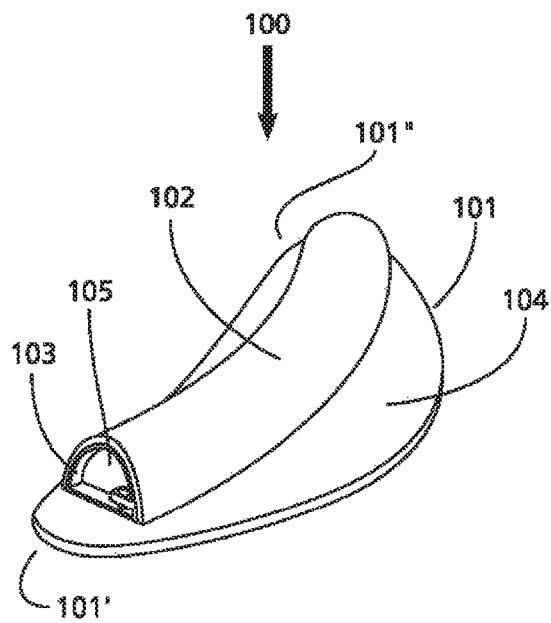
FIG. 1 is a perspective view of any exemplary embodiment of a nasal splint.

FIG. 1 is a perspective view of an exemplary embodiment of a nasal splint 100 that includes a member 101, tubular airway 102, and structure 103. The member 101 may be a sheet formed in relatively flat configuration having a wall thickness and including a first outer planar surface 104 and a second outer planar surface (not shown) located opposite the first outer planar surface 104. The member 101 may optionally include at least one hole (not shown) extending between first outer planar surface 104 and its second outer planar surface.

The tubular airway 102 is configured as an elongated component having a wall joined to the first outer planar surface 104 or sharing a wall with the member 101 and positioned in such a way that it is substantially parallel to the first outer planar surface 104 of the member 101. The tubular airway 102 is also aligned in a direction along a longitudinal axis extending from a first end 101' of the member 101 to a second end 101" of the member 101. The tubular airway 102 may further include at least one lumen 105 extending through the tubular airway 102. The tubular airway 102 may be formed in various shapes, such as substantially circular, semi-circular, oval, half oval, rectangle, square, or other shapes that provide an opening along its length.

Figure 2:
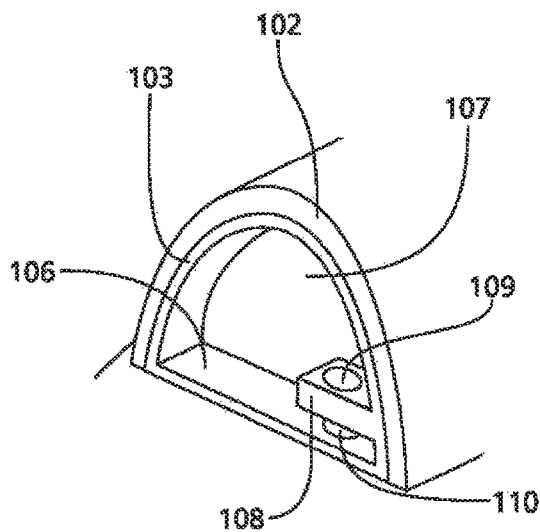
FIG. 2 is a detailed view of a distal section of the nasal splint shown in FIG. 1.

FIG. 2 is a perspective view of the structure or suture receptacle 103 of the nasal splint 100. The structure 103 may include a rim 106, lumen or aperture 107, and a suture bracket 108 extending some distance into the lumen 107. The suture bracket 108 may include a hole 109 sized to accommodate various sizes of suture needles and gages or diameters of suture thread. The structure 103 may further include a second hole 110 disposed in the rim 106 that is generally concentrically aligned with the hole 109 of the suture bracket 108, and is situated adjacent to the first outer planar surface 104 of the member 101. The hole 110 may further be sized to accommodate various sizes of suture needles and gages/diameters of suture thread.

Figure 3A:
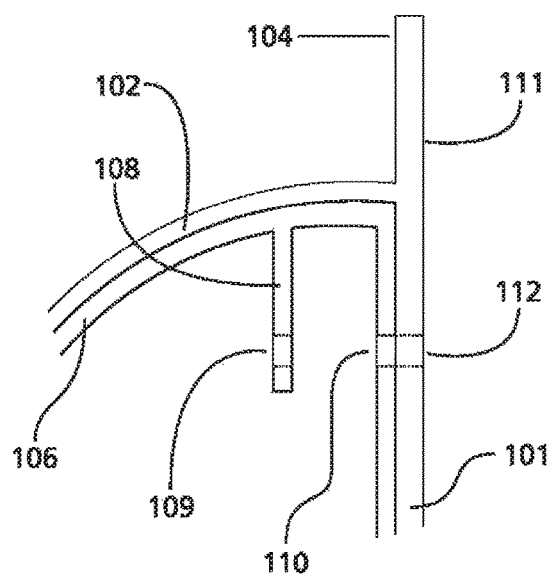
FIGS. 3A and 3B are cross-sectional details of the distal section of the nasal splint shown in FIGS. 1 and 2.
Figure 3B:
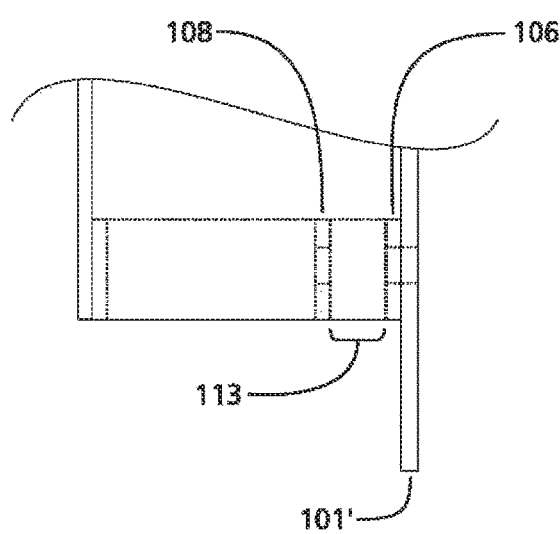

FIGS. 3A and 3B are front and top views, respectively, of a distal section of the nasal splint 100 of FIG. 1. FIGS. 3A and 3B show the second outer planar surface 111 of the member 101 and a hole 112 crossing through the wall of the member 101 extending between the first outer planer surface 104 and the second outer planar surface 111. In this example, the hole 112 is sized similarly to and aligned concentrically with holes 110 and 109. The space 113 between the suture bracket 108 and the rim 106 of the structure 103 may be sized to facilitate using various cutting instruments known in the art including, but not limited to scalpels, razor/razor blades, surgical scissors, and the like (not shown).

Figure 4A:
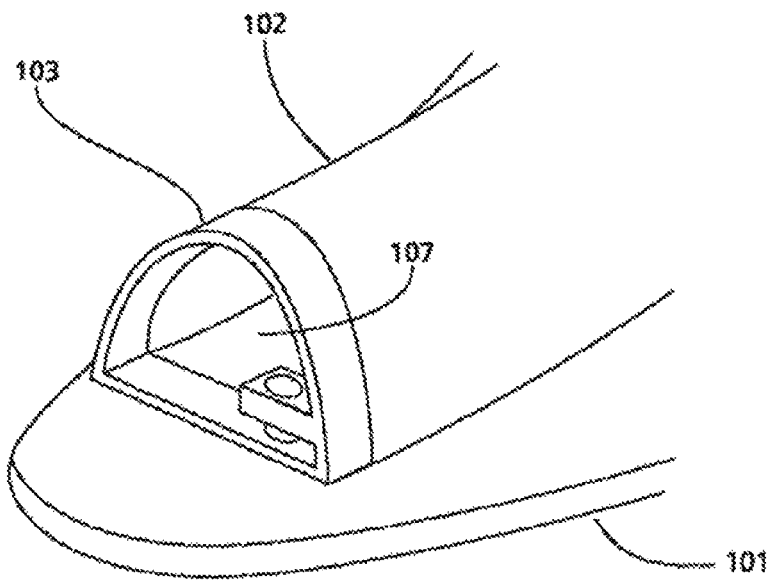
FIGS. 4A and 4B are perspective views of a distal section of alternative embodiments of a nasal splint similar to that shown in FIG. 1.
Figure 4B:
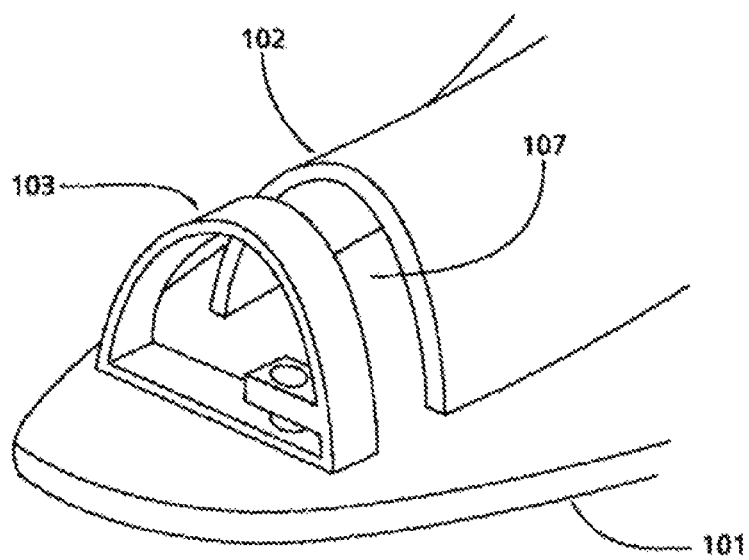

While the nasal splint 100 shown in FIGS. 1-3 includes holes 109, 110 and 112 that are depicted as circular and of identical diameters, it should be clear to one of skill in the art that each of these holes may have different sizes and/or geometries including, but not limited to ellipses, polygons, and the like. Furthermore, the hole 112 may be omitted in other embodiments of the nasal splint (not shown). If the hole 112 is omitted, the material of the member 101 itself may be chosen to enable penetration using a suture needle (not shown) and/or the material may have a thin or otherwise weakened region (not shown), thereby facilitating creating a puncture hole with the functionality of the hole 112 as a result of this penetration. The material may include but not be limited to medical grade versions of silicone rubber, latex, polyurethane, PEBAX and the like. Similarly, while the structure 103 is shown as fitting within the lumen 105 of the tubular airway 102, the structure 103 may optionally be placed directly adjacent to the distal edge of the tubular airway 102, e.g., as shown in FIG. 4A, or offset distally from the distal edge of the tubular airway 102, e.g., as shown in FIG. 4B, which may maximize the internal cross sectional area of the tubular airway 102, as well as the cross sectional area of the lumen 107 of the structure 103.

Figure 5A:
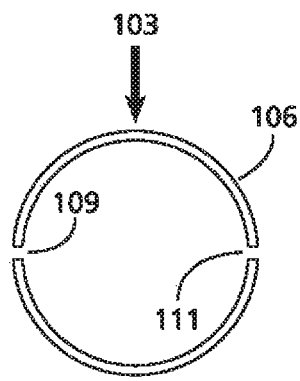
FIGS. 5A-5I are cross-sectional views of alternative embodiments of a structure subcomponent that may be included in a nasal splint.
Figure 5B:
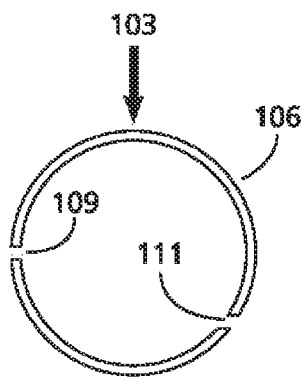

FIGS. 5A through 5I depict cross-sectional views of alternative embodiments of structure 103 that may be included in a nasal splint, such as that shown in FIG. 1. In FIGS. 5A through 5I, the varying structures 103 are assumed to be intended for use in a nasal splint that is to be placed in the right nasal cavity of a patient (i.e., the member 101 is located to the right of the structure 103). Structures 103 that are intended for use in a nasal splint that are to be placed in the left nasal cavity of a patient would be mirror reflections of the depicted structures 103 about a vertical plane located to the right of the structures. FIG. 5A depicts holes 109 and 111 located in the rim 106 in a symmetric configuration about the midline of structure 103. FIG. 5B depicts holes 109 and 111 located in the rim 106 in an asymmetric configuration about the midline of structure 103. While FIGS. 5A and 5B depict holes 109 and 111 on opposite sides of the midline of structure 103, it should be clear to one of skill in the art that this is merely exemplary and the holes 109 and 111 may be located at any point around the rim 106. Furthermore, it should be clear that additional holes in the structure 103 are contemplated, and that these additional holes may be of any size or shape, and in any location in the structure 103.

Figure 5C:
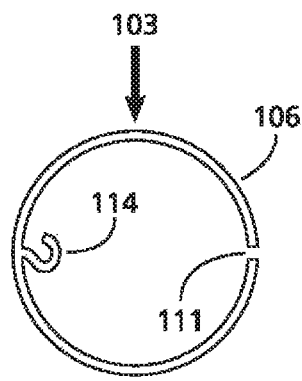

FIG. 5C depicts a hook 114 extending from the inner surface of the rim 106 at a location opposite of the hole 111 in the structure 103. The opening of the hook 114 faces the top of the structure 103, e.g., to facilitate the placement of suture thread (not shown) over the hook 114 and through the hole 111. The inclusion of the hook 114 may provide benefits to the surgeon, e.g., facilitating advancing the suture thread across the lumen of the structure 103, as it may reduce the number of times the suture needle would need to traverse a hole. Looping suture thread over the hook 114 may be preferable to passing a suture needle through the hole 109, e.g., as depicted in FIGS. 5A and 5B.

Figure 5D:
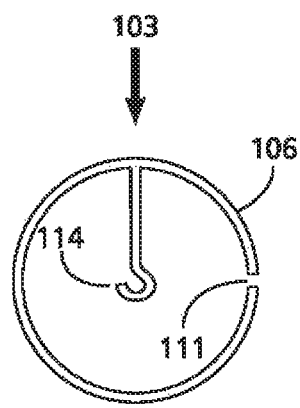

It should be noted that other locations and orientations of the hook 114 are contemplated. For example, the hook 114 may be located at any position within the rim 106 and/or in any orientation that facilitates the placement of suture thread across the lumen of the structure 103. One example is shown in FIG. 5D; in this embodiment of the structure 103, the hook 114 is suspended from the interior of the rim 106 at a location about ninety degrees (90°) relative to the hole 111 and oriented with the opening of the hook 114 facing away from the hole 111.

FIGS. 5A through 5D depict the structure 103 as a closed ring configuration. The use of a circular structure is beneficial in that it may provide support to the tubular airway 107 when the suture thread is cinched or drawn tight during knot placement, e.g., preventing or mitigating collapse of either the structure 103 or the tubular airway 107 when the suture thread is actively tensioned or passively maintained in tension. Furthermore, the relatively wide lumen provides a large aperture that the suture thread is required to cross; this presents the surgeon with a more apparent, easier target to access and cut when the nasal splint is ready to be removed.

Figure 5E:
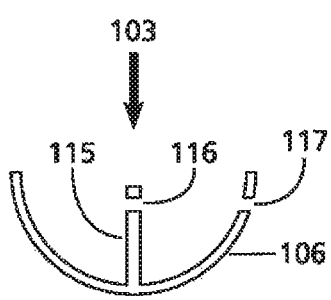
Figure 5F:
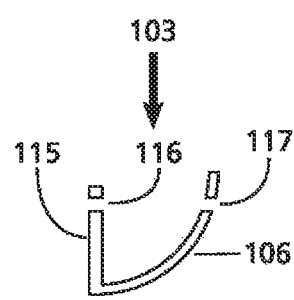

Other geometries of structure 103 are contemplated, such as that shown in FIG. 5E. The configuration of the structure 103 shown in FIG. 5E is generally semi-circular in shape, with the inclusion of a suture bracket 115 extending inward from the internal surface of the rim 106 and including a hole 116. The suture bracket 115 is located at the midline of the structure 103 and shown to be extending towards the center point of the semi-circular rim 106. It is also contemplated that the suture bracket 115 may be located at any position within the boundary of the rim 106, and/or that the suture bracket 115 may also extend radially towards the center of the semi-circle outlined by the rim 106 or may extend towards the open space or area covered (or encased) within the rim 106. It should be clear to one of skill in the art that the suture bracket 115 may extend any distance towards the center or open space of structure 103. The rim 106 further includes a hole 117 located near one of the end of the rim 106. While the holes 116 and 117 are depicted at similar in size and shape, it should be clear to one of skill in the art that the holes 116 and 117 may vary in size and or shape independently of each other. Likewise, the location of the hole 116 in the suture bracket 115 and the location of the hole 117 in the rim 106 may vary from that shown in FIG. 5E. For example, the embodiment of FIG. 5F is identical to FIG. 5E, except that the configuration of the rim 106 is a quadrant.

Figure 5G:
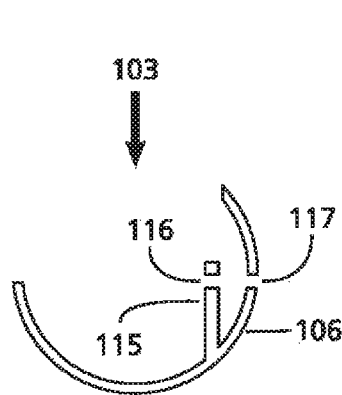

FIG. 5G depicts a cross-section of another exemplary structure 103 where the rim 106 is an arc greater than a semi-circle. The structure 103 further includes a suture bracket 115 extending inward from the internal surface of the rim 106 and further including a hole 116. The suture bracket 115 is located to the right of the midline of the rim 106 and is depicted as projecting towards the end of the rim 106. The rim 106 further includes a hole 117 located near one end of the suture bracket 115. While the holes 116 and 117 are depicted as similar in size and shape, it should be clear to one of skill in the art that the holes 116 and 117 may have different sizes and/or shapes than each other. Likewise, the location of the hole 116 in the suture bracket 115 and the location of the hole 117 in the rim 106 may vary from that shown in FIG. 5G.

Figure 5H:
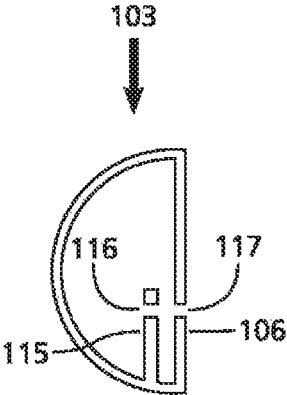

FIG. 5H depicts an exemplary configuration of a structure 103 where the rim 106 approximates the general shape of the letter "D", with the flat side of the rim 106 substantially parallel to the member 101 (e.g., as shown in FIGS. 1 and 2). The structure 103 further includes a suture bracket 115 extending inward from the internal surface of the rim 106 and further including a hole 116. The rim 106 further includes a hole 117 located to the right of the suture bracket 115. While the holes 116 and 117 are depicted as similar in size and shape, it should be clear to one of skill in the art that holes 116 and 117 may have different sizes and/or shapes than each other. Likewise, the location of the hole 116 in the suture bracket 115 and the location of the hole 117 in the rim 106 may vary from that shown in FIG. 5H.

Figure 5I:
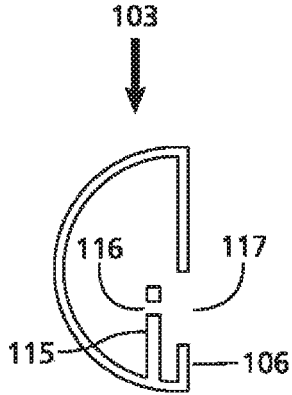

FIG. 5I depicts a cross-section of another exemplary structure 103 where the rim 106 generally approximates the shape of the letter "D," with the flat side of the rim 106 substantially parallel to the member 101 (not shown). The structure 103 further includes a suture bracket 115 extending inward from the internal surface of the rim 106 and further including a hole 116. The rim 106 further includes a hole 117 located along the flat side of the structure 103. In this embodiment, the hole 117 is larger than the hole 116, and may be circular, channel-like, or some other shape.

It should be noted that the features described for one particular embodiment of the structure 103 (e.g., the hook 114 shown in FIG. 5C) may be combined with any of the other features or structures 103 described elsewhere herein. For example, a feature such as the hook 114 shown in FIG. 5C may replace the hole 116 in FIG. 5F. All permutations of shapes and sizes of the structure 103, holes, hooks, features and other elements of the structure 103 are contemplated.

Figure 6A:
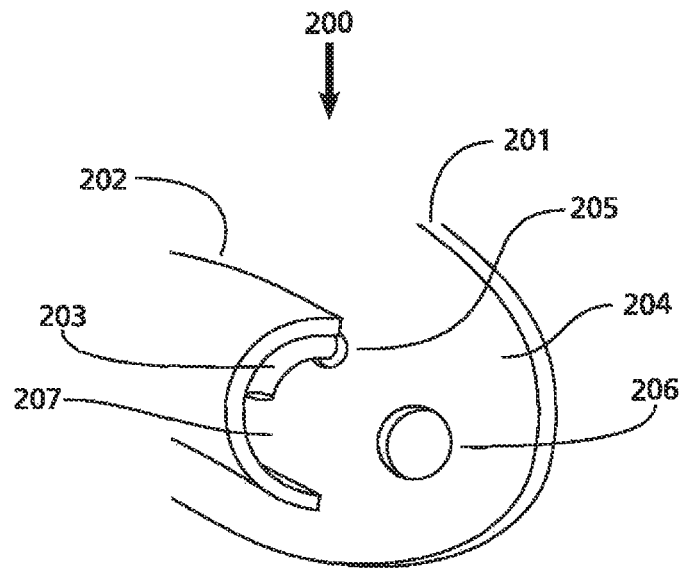
FIGS. 6A and 6B show perspective views of a distal section of alternative embodiments of a nasal splint.

FIG. 6A depicts a perspective view of the distal portion of another exemplary embodiment of a nasal splint 200 including a member 201, tubular airway 202, and structure 203. The member 201 may include a sheet formed in relatively flat configuration having a wall thickness with a first outer planar surface 204 and a second outer planar surface (not shown) located opposite the first outer planer surface 204. The member 201 further includes holes 205 and 206 extending between the first outer planar surface 204 and the second outer planar surface (not shown). The tubular airway 202 may be constructed and/or configured similar to other embodiments herein, such as that shown in FIGS. 1 and 2.

The structure 203 resides within the lumen 207 of and is joined to the tubular airway 202. In this embodiment, the structure 203 is a closed tube extending in an arc that conforms to the cross-section of the tubular airway 202, e.g., originating from the base end of the tubular airway 202 and terminating at a length that fills the quadrant of the interior surface of the tubular airway 202, and sized to accept standard sizes of suture needles. The hole 205 is concentrically aligned with the end opening of the structure 203 and the hole 206 is located near the distal end of the tubular airway 202.

While the hole 206 is depicted as being larger in diameter than the hole 205, it should be noted that the sizes of the holes 205 and 206 may be different than one another. Also, while the holes 205 and 206 are illustrated to be circular in shape, other shapes may be provided including but not limited to ellipses, polygons, and the like are contemplated. Furthermore, while FIG. 6A shows a pair of holes 205 and 206, embodiments of the nasal splint 200 are contemplated that have zero, one, or more holes in the member 201. In an exemplary embodiment with zero holes, it is contemplated that the member 201 may be constructed from materials and/or may include thinner or weaker regions (not shown) that enable penetration by suture needles with suture, wherein the functionality provided by the hole 206 may be provided by the hole created by the needle penetration.

Figure 6B:
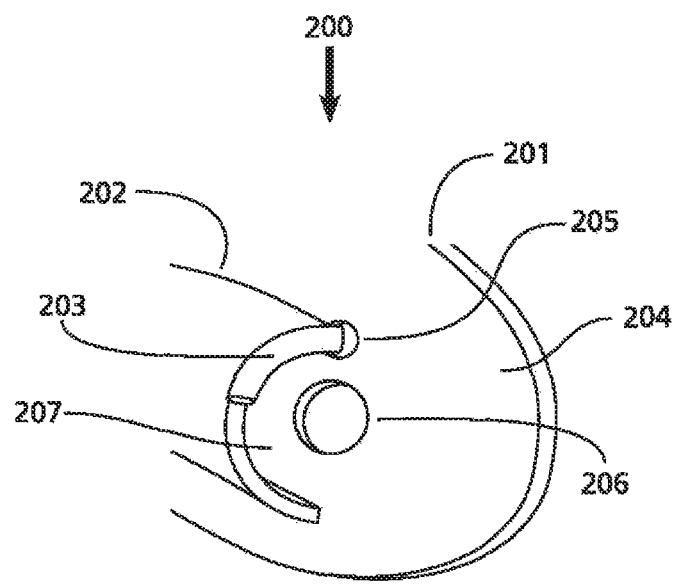

FIG. 6B depicts a perspective view of the distal portion of another example of a nasal splint 200 including a member 201, tubular airway 202, and structure 203, generally similar to that described with reference to FIG. 6A. In this example, the structure 203 is larger and situated at the distal edge and directly adjacent to the tubular airway 202. This orientation (in comparison to the example shown in FIG. 6A) increases the space in the lumen of the tubular airway 202, e.g., allowing improved (i.e., less restricted) passage of air through the lumen when the patient receiving the nasal splint breathes.

The member 201 further includes holes 205 and 206 extending through the wall between the first outer planer surface 204 and the second outer planar surface (not shown). The hole 205 is concentrically aligned with the end opening of the structure 203. The hole 206 is located in the member 201 such that a line drawn perpendicular to the bottom opening of the structure 203 passes through the center point of the hole 206.

FIG. 7A depicts a perspective view of the distal portion of still another embodiment of a nasal splint 300 including a member 301, tubular airway 302, and structure 303. The member 301 is a sheet formed in relatively flat configuration having a wall thickness and comprises a first outer planar surface 304 and a second outer planar surface (not shown) located opposite the first outer planer surface 304, and a hole 307 situated distal to the structure 303 and crossing through the wall of the member 301.

The tubular airway 302 is configured as an elongated component having a wall joined to the first outer planar surface 304 and situated such that it is substantially parallel to the member 301. The tubular airway 302 is also aligned at a direction along a longitudinal axis extending from a first end of the member 301 to a second end of member 301 (not shown). The structure 303 is a U-shaped bracket further including holes 305 and 306. The structure 303 is offset distally from the distal end of the tubular airway 302 and joined to the member 301 such that the holes 305 and 306 are substantially perpendicular to the first outer planar surface 304 of the member 301. While the holes 305, 306, and 307 are illustrated to be circular in shape, other shapes may be provided including but not limited to ellipses, polygons, and the like. While the member 301 is shown with a single through hole 307, it should be noted that the incorporation of additional holes into the member 301 is also contemplated.

FIGS. 7B and 7C depict front and side views, respectively, of the structure 303 shown in FIG. 7A.

It should be clear to one of skill in the art that various permutations of the examples shown are contemplated, such as a combination of the member 301 and structure 303 shown in FIGS. 7A through 7C with the tubular airway 102 shown in FIGS. 1-4. Any combination of member, tubular airway, and structure disclosed herein are contemplated.

Figure 8A:
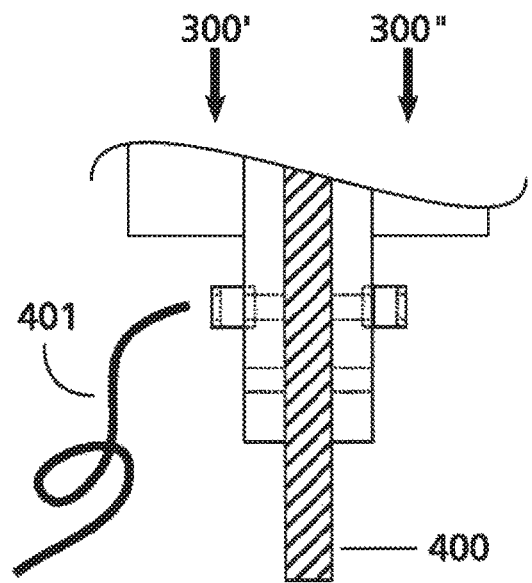
FIGS. 8A-8D are top views showing a method for securing two splints to a nasal septum of a patient.
Figure 8B:
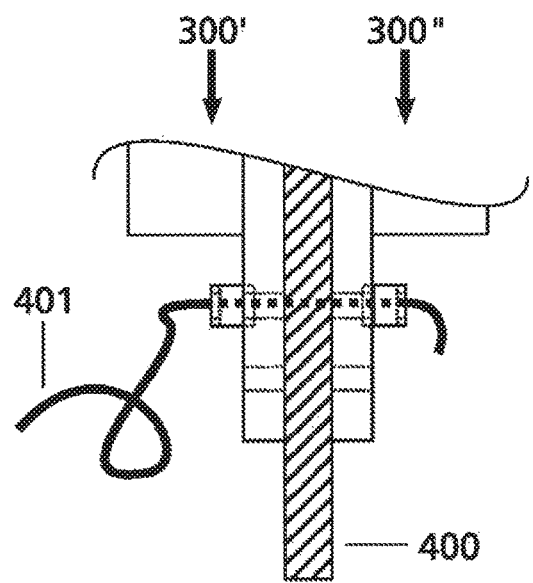
Figure 8C:
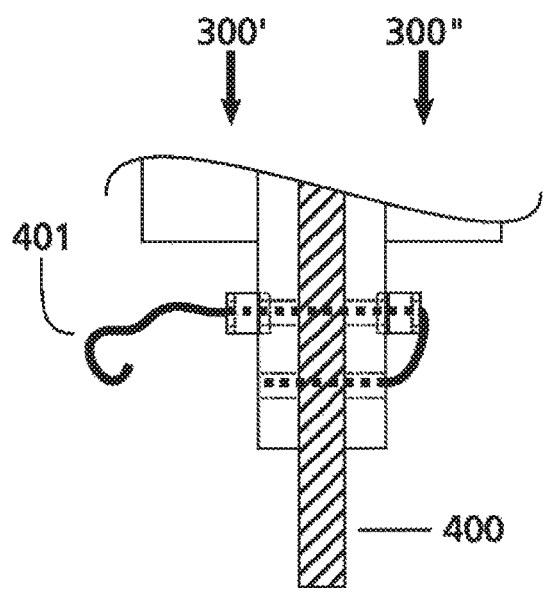

FIGS. 8A-8E depict top views of a pair of exemplary nasal splints 300' and 300" (which may be any of the embodiments herein) as they may be used to stabilize the nasal septum 400 after a procedure, such as a septoplasty. FIG. 8A depicts the two nasal splints 300' and 300" in position on the right side and left side of the nasal septum 400, respectively, and a suture needle (not shown for clarity) with a length of suture thread 401. FIG. 8B shows the suture thread 401 drawn through the proximal set of holes in the right nasal splint 300,' across the nasal septum 400, and out the proximal set of holes in the left nasal splint 300." FIG. 8C shows the suture thread 401 reversed and returned to the opposite side through the distal hole in the left nasal splint 300," across the nasal septum 400, and out of the distal hole in the right nasal splint 301.'

Figure 8D:
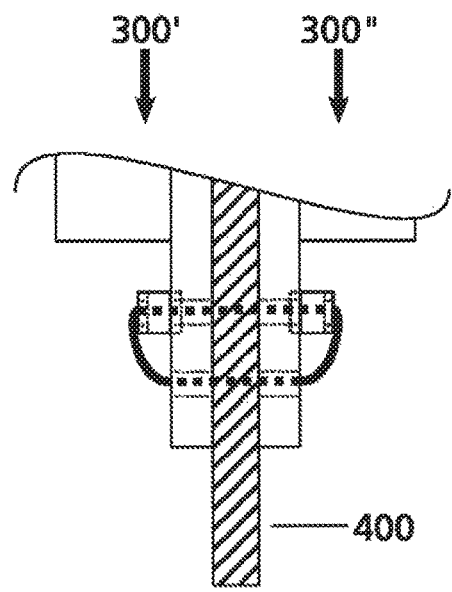
Figure 8E:
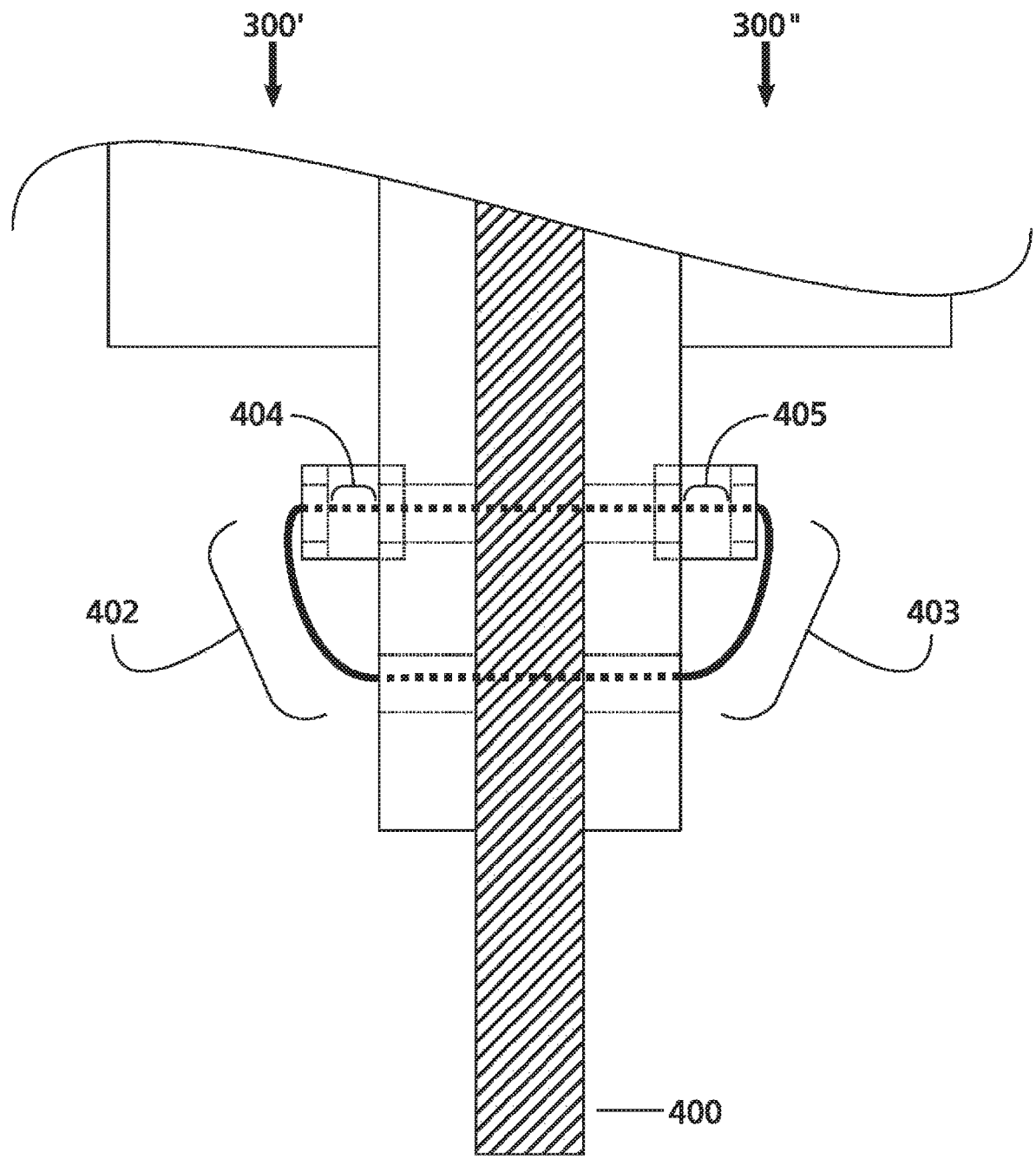
FIG. 8E is a top view of splints from the method shown in FIGS. 8A-08D secured to the nasal septum illustrating segments of suture that are available for cutting.

FIG. 8D shows the end result when a knot (not shown) is cinched or tensioned using the suture thread 401 to hold or secure the nasal splints 301' and 301" in the nasal cavity to provide post-surgical splinting and support of the nasal septum 400. FIG. 8E is a magnified view of FIG. 8D showing four elevated and/or exposed/accessible segments 402, 403, 404, and 405 of suture 401 that are available to be cut when the nasal splints 300' and 300" are ready to be removed from the patient at follow up.

Figure 9:
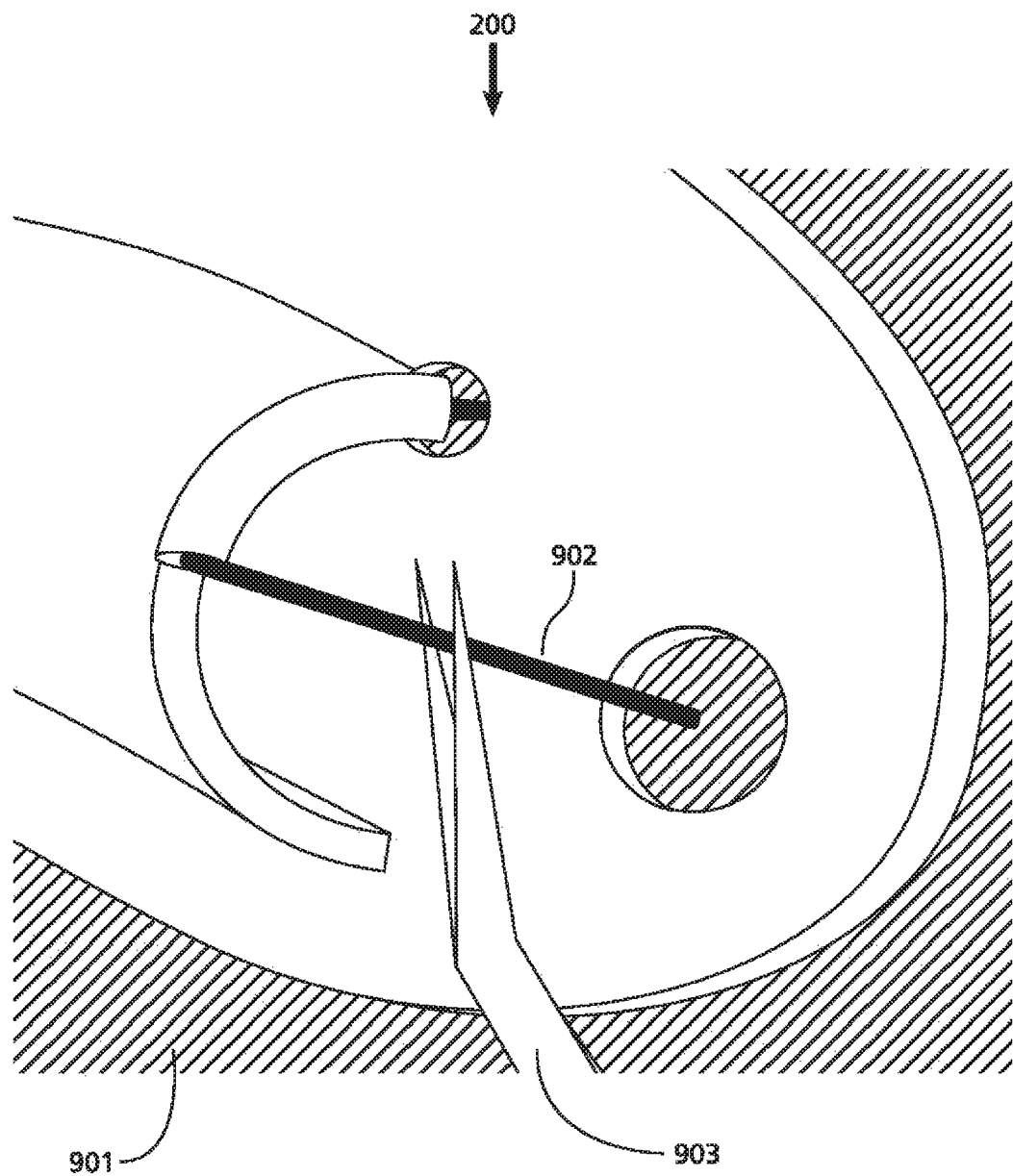
FIG. 9 is a perspective view showing a method for using a cutting instrument (i.e., a pair of surgical scissors) to cut a suture holding an embodiment of a nasal splint against the nasal septum.

FIG. 9 depicts a perspective view of an exemplary nasal splint 200 (e.g., the nasal splint shown in FIGS. 6A and 6B) placed in position against the nasal septum 901 (indicated by the hashed background) and secured in place with suture 902. In this illustration, a cutting instrument 903 may be oriented about suture 902 to allow it to be cut or released when the nasal splint 200 is ready to be removed at follow up. While FIG. 9 depicts the cutting instrument 903 as a pair of surgical scissors, it should be clear to once of skill in the art that any implement capable of cutting the suture 902 may be used to perform that function.

The preceding merely illustrates the principles of the invention. It will be appreciated that those skilled in the art will be able to devise various arrangements which, although not explicitly described or shown herein, embody the principles of the inventions and are included within its scope. Furthermore, all examples and conditional language recited herein are principally intended to aid the reader in understanding the principles of the inventions and the concepts contributed by the inventors to furthering the art, and are to be construed as being without limitation to such specifically recited examples and conditions. Moreover, all statements herein reciting principles, aspects, and embodiments of the inventions as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope of present invention is embodied by the appended claims.

We claim:

1. A method for treating a patient, comprising:
    inserting a nasal splint into the patient's sinus, the nasal splint comprising an elongate planar member and an airway lumen extending along a first surface of the elongate member;
    positioning a second surface of the elongate member against the sinus septum such that the airway lumen extends along the patient's sinus; and
    directing a suture through the patient's septum, the elongate member, and a structure on the nasal splint such that the suture extends across a portion of the airway lumen,
    wherein the structure comprises a bracket on the nasal splint that is spaced apart from the first surface adjacent an opening in the airway lumen.

2. The method of claim 1, further comprising:
    inserting a cutting instrument into the portion of the airway lumen;
    cutting the suture; and
    removing the nasal splint.

3. The method of claim 1, wherein the nasal splint comprises a first nasal splint, the method further comprising:
    inserting a second nasal splint into the patient's sinus opposite the nasal septum from the first nasal splint, the second nasal splint comprising an elongate planar member, an airway lumen extending along a first surface of the elongate member; and
    positioning a second surface of the elongate member of the second nasal splint adjacent the sinus septum such that the airway lumen extends along the patient's sinus,
    wherein directing a suture through the patient's septum further comprises directing the suture through the first and second nasal splints and the nasal septum such that the suture extends across a portion of the airway lumen of each of the first and second nasal splints.

4. The method of claim 1, wherein the structure comprises a hole adjacent the bracket.

5. A method for performing a medical procedure, comprising:
    removing a suture from a nasal splint securing the nasal splint within a patient's sinus, wherein the suture traverses an aperture in a nasal splint, wherein prior to removing the suture, a space is present between the suture and a first planar surface of the nasal splint, and a structure on the nasal splint creates the space, and
    wherein removing the suture comprises inserting a cutting instrument into the space and cutting the suture to facilitate release of the suture and removal of the splint from the patient's sinus.

6. The method of claim 5, wherein the structure comprises a tubular passage connected to a first edge of a tubular airway connected to the nasal splint.

7. The method of claim 5, wherein the structure comprises an annular ridge connected to the first planar surface of the nasal splint.

8. The method of claim 5, wherein a portion of the nasal splint is more rigid than a remainder of the nasal splint.

9. The method of claim 5, wherein the structure comprises a bracket on the nasal splint that is spaced apart from the first surface adjacent an opening in an airway lumen of the nasal splint.

10. The method of claim 9, wherein the bracket is located adjacent a hole through the nasal splint.

11. A method for treating a patient, comprising:
inserting a nasal splint into the patient's sinus, the nasal splint comprising an elongate planar member, an airway lumen extending along a first surface of the elongate member;
positioning a second surface of the elongate adjacent the sinus septum such that the airway lumen extends along the patient's sinus; and
directing a suture through the patient's septum and two locations on the elongate member such that the suture extends at least partially across the airway lumen,
wherein one of the two locations comprises a bracket on the nasal splint that is spaced apart from the first surface adjacent an opening in the airway lumen.

12. The method of claim 11, further comprising:
inserting a cutting instrument into the portion of the airway lumen;
cutting the suture; and
removing the nasal splint.

13. The method of claim 11, further comprising:
inserting a cutting instrument into the portion of the airway lumen;
cutting the suture; and
removing the nasal splint.

14. The method of claim 11, wherein the nasal splint comprises a first nasal splint, the method further comprising:
inserting a second nasal splint into the patient's sinus opposite the nasal septum from the first nasal splint, the second nasal splint comprising an elongate planar member, an airway lumen extending along a first surface of the elongate member; and
positioning a second surface of the elongate member of the second nasal splint adjacent the sinus septum such that the airway lumen extends along the patient's sinus,
wherein directing a suture through the patient's septum further comprises directing the suture through the first and second nasal splints and the nasal septum such that the suture extends across a portion of the airway lumen of each of the first and second nasal splints.

15. The method of claim 11, wherein one of the two locations comprises a hole through the nasal splint adjacent to the bracket.

16. The method of claim 11, wherein one of the two locations comprises a hole through the nasal splint adjacent an opening in the airway lumen.

* * * * *